United States Patent [19]

Pruett et al.

[11] 4,301,086

[45] Nov. 17, 1981

[54] BIMETALLIC CLUSTERS OF RUTHENIUM WITH COPPER, SILVER AND GOLD

[75] Inventors: Roy L. Pruett, New Providence; John S. Bradley, Scotch Plains, both of N.J.

[73] Assignee: Exxon Research & Engineering Co., Florham Park, N.J.

[21] Appl. No.: 135,998

[22] Filed: Mar. 31, 1980

[51] Int. Cl.³ .............................................. C07F 1/08
[52] U.S. Cl. ........................... 260/438.1; 252/431 N; 260/429 R; 260/430
[58] Field of Search ................ 260/429 R, 430, 438.1

[56] References Cited

U.S. PATENT DOCUMENTS

```
3,786,132  1/1974  Dawes et al. ................... 260/429 R
3,793,355  2/1974  Wilkinson ...................... 260/429 R
3,989,799  11/1976 Brown .......................... 260/429 R X
4,115,428  9/1978  Vidal et al. .................... 260/449 L
4,115,433  9/1978  Cosby et al. ................... 260/429 R X
```

OTHER PUBLICATIONS

J. C. S. Dalton, pp. 52-54, (1980).
J. Organometallic Chem. 180, C33-C35, (1980).

*Primary Examiner*—Helen M. S. Sneed
*Attorney, Agent, or Firm*—James H. Takemoto

[57] ABSTRACT

This invention relates to new bimetallic cluster compounds of the formula $$L_2M_2Ru_6C(CO)_{16}$$

wherein L is RCN, R being $C_1$ to $C_6$ alkyl, $C_6$ to $C_{10}$ aralkyl or phenyl, and M is copper, silver or gold. These compounds are useful as homogeneous catalysts for converting synthesis gas to methanol.

7 Claims, 1 Drawing Figure

⊗ = Cu

● = Ru

BIMETALLIC CLUSTERS OF RUTHENIUM WITH COPPER, SILVER AND GOLD

BACKGROUND OF THE INVENTION

1. Field of the Invention

This invention relates to a bimetallic cluster compound. More particularly, the bimetallic cluster compound contains ruthenium and a Group Ib metal.

2. Description of the Prior Art

A rhodium carbonyl carbide cluster compound is described in U.S. Pat. No. 4,115,428. Mixed metal triaconta carbonyl salt clusters which may contain ruthenium or Group Ib metals are known from U.S. Pat. Nos. 3,989,799 and 3,974,259. Other ruthenium complexes which may contain carbonyls are described in U.S. Pat. Nos. 3,793,355 and 3,786,132.

SUMMARY OF THE INVENTION

The present invention is directed to the discovery of novel bimetallic cluster compounds containing ruthenium and a group Ib metal. The new compositions of matter comprise a bimetallic cluster compound of the formula $$L_2M_2Ru_6C(CO)_{16}$$

wherein L is RCN, R being $C_1$ to $C_6$ alkyl, $C_6$ to $C_{10}$ aralkyl or phenyl and M is copper, silver or gold.

An X-ray structural determination of the compound where L is $CH_3CN$ and M is copper indicates the presence of a Cu-Cu bond as well as Cu-Ru bonds. Such a Cu-Cu bond is very unusual in view of the octahedral arrangement of the Ru atoms within the crystal lattice. It would be expected that the Cu atoms should occupy opposite faces of the octahedral cluster of ruthenium atoms.

DETAILED DESCRIPTION OF THE INVENTION

Figure 1:
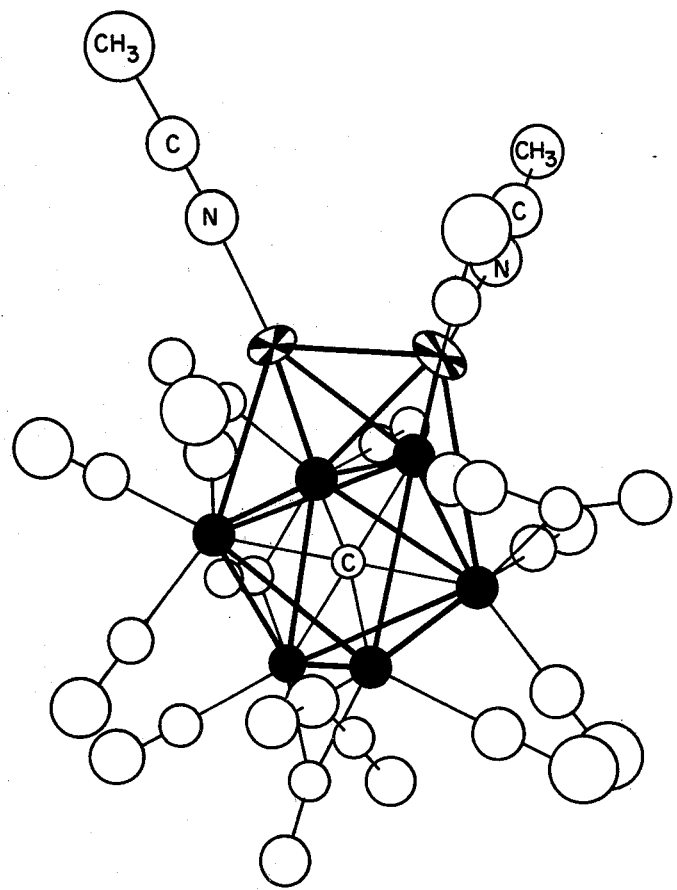
FIG. 1 is a schematic showing the crystal structure of $(CH_3CN)_2Cu_2Ru_6C(CO)_{16}$.

The instant bimetallic cluster compounds are derived from a ruthenium carbidocarbonyl cluster anion of the formula $Ru_6C(CO)_{16}{}^{2-}$ and a Group Ib metal cation, i.e., $Cu^+$, $Ag^+$ or $Au^+$, possess a Ru to Group Ib metal ratio of 3:1, and are soluble in alcohols, ketones, ethers, aliphatic, alicyclic and aromatic hydrocarbons. The solubility behavior is indicative of the presence of covalent bonding in spite of the formal +1 oxidation state of the Group Ib metal.

In the bimetallic cluster of the general formula $L_2M_2Ru_6C(CO)_{16}$, L is preferably $CH_3CN$, $CH_3CH_2CN$, $CH_3CH_2CH_2CN$, $(CH_3)_2CHCN$, $\phi CH_2CN$ or $\phi CN$ ($\phi$ = phenyl), especially $CH_3CN$, and M is preferably copper. One preferred embodiment of the bimetallic cluster has the formula $$(CH_3CN)_2Cu_2Ru_6C(CO)_{16}$$

Other preferred embodiments include:

$$(CH_3CN)_2Ag_2Ru_6C(CO)_{16}$$

$$(CH_3CN)_2Au_2Ru_6C(CO)_{16}$$

Moreover, the nitrile moiety in $L_2M_2Ru_6C(CO)_{16}$ (L=RCN) can be replaced via a ligand exchange reaction. Thus L can also be, e.g., sulfides, carbon monoxide, amines, phosphines and ethers.

Ruthenium carbidocarbonyl cluster anions of the formula $$[Ru_6C(CO)_{16}]^{2-}$$

are prepared by the reaction between $[MnCO_5]^-$ and $Ru_3(CO)_{12}$ in a high boiling ether. The corresponding cation in the carbidocarbonyl cluster anion is not critical and may be any cation such as alkali metal, alkaline earth, $N(R^1)_4{}^+$, $P(R^1)_4{}^+$ or $As(R^1)_4{}^+$ where $R^1$ is alkyl or aryl, and the like.

Bimetallic cluster compounds are prepared by reacting a solution of a ruthenium carbidocarbonyl cluster anion in an inert organic solvent with a Group Ib metal cation of the formula $M(L_4)^+$ where L is RCN, R being defined above with the proviso that the Group Ib salt is soluble in the solvent employed. Examples of suitable organic solvents include alcohols, ketones and ethers. The anion associated with the Group Ib metal cation is not critical and may be any anion such as halide, $SO_4{}^-$, $BF_4{}^-$, $PO_4{}^-$, $NO_3{}^-$, and the like. The reaction preferably is carried out in the absence of $O_2$. A typical reaction is set forth as follows:

$$(Et_4N)^+{}_2[Ru_6C(CO)_{16}]^{2-} + 2[Cu(CH_3CN)_4]^+BF_4{}^- \rightarrow (CH_3CN)_2Cu_2Ru_6C(CO)_{16} + 6CH_3CN + 2Et_4N^+BF_4{}^-$$

The reaction mixture is stripped of solvent, washed with water to remove any inorganic salts, dried and recrystallized.

The structure of the bimetallic cluster compounds of the invention may be ascertained by X-ray crystal diffraction studies. FIG. 1 illustrates the crystal structure determined for $(CH_3CN)_2Cu_2Ru_6C(CO)_{16}$. The structure is unusual in that there is a Cu-Cu bond which is not bridged by a ligand. In FIG. 1, the Cu-Cu bond length is 2.689Å which is similar to other reported Cu-Cu bonds, e.g., Bezman et al. (J. Am. Chem. Soc. 93, 2063 (1971)) report a Cu-Cu bond length of 2.65 Å in $Cu_6(P\phi_3)_6H_6$, and the Cu-Ru bond length is 2.57–2.72 Å. The carbide in the center of the $Ru_6$ cluster has Ru-C=2.04 Å. The infrared spectrum is characterized by bands at 2070(m), 2030(s), 1998(sh), 1948(sh), and 1850(br)cm$^{-1}$.

Compositions according to the present invention are useful in a homogeneous catalytic system for the preparation of methanol from CO and $H_2$. This reaction is of interest since Cu modifies Ru in the bimetallic cluster compound. Both Cu and Ru are known hydrogenation catalysts but do not normally yield the same products.

The homogeneous process for converting CO and $H_2$ to methanol comprises contacting CO and $H_2$ in a CO:$H_2$ ratio of from 0.1 to 2, preferably 0.5 to 1 at a pressure of from 1 to 150 MPa, preferably 40 to 100 MPa in the presence of a catalytically effective amount of bimetallic cluster compound of the formula $L_2M_2Ru_6C(CO)_{16}$ where L is defined as above and M is copper, silver or gold, preferably copper. The amount of bimetallic cluster compound is from 0.0001 to 0.1 M. Any organic solvent which is inert under the reaction conditions may be employed.

The composition and process for preparing methanol are further illustrated in the following examples.

EXAMPLE 1

A ruthenium carbidocarbonyl salt of the formula $(Et_4N)_2{}^+[Ru_6C(CO)_6]^{2-}$ is prepared by the reduction of $Ru_3(CO)_{12}$ with $Mn(CO)_5{}^-$ in refluxing diglyme. 5 g of $Ru_3(CO)_{12}$ was added to a solution of 3 g $NaMn(CO)_5$ in 150 ml dry diglyme. The resulting mixture was refluxed under nitrogen for several hours. A red solution formed and the desired product could be obtained by adding $(Et_4N)^+Cl^-$. The infrared spectrum of the recrystallized product shows bands at 2048(w), 2042(w), 1977(s), 1952(sh), 1918m, 1820(sh) and 1780m $cm^{-1}$. Further details are given in J. Organomet. Chem., 184, C33-C35 (1980).

EXAMPLE 2

In order to prepare the bimetallic cluster compound $(CH_3CN)_2Cu_2Ru_6C(CO)_{16}$, an acetone solution of $(Et_4N)_2{}^+[Ru_6C(CO)_{16}]^{2-}$ is added to a solution of $Cu(CH_3CN)_4{}^+BF_4{}^-$ also in acetone. The course of the reaction may be followed using infrared spectroscopy to study the carbonyl band of the ruthenium carbido carbonyl cluster. This spectroscopic investigation indicates a quantitative formation of the instant bimetallic cluster compounds as indicated by the change in the infrared spectral region for carbonyl stretching frequencies.

$(CH_3CN)_2Cu_2Ru_6C(CO)_{16}$ is isolated and purified by filtering the reaction mixture to remove inorganic salts, stripping the acetone solvent and recrystallization from acetone.

The crystal structure as determined from a single crystal study on a Enraf-Nonius CAD 4 diffractometer is shown in FIG. 1. The subject compound crystallizes in the triclinic space group $\overline{P}_1$, with cell constants a=10.122, b=16.364, c=9.874, $\alpha=97.35$, $\beta=96.58$, $\gamma=77.89$ with a refinement of the structure to R=0.059.

EXAMPLE 3

A high pressure reactor containing a solution of 0.6 g. of $(CH_3CN)_2Cu_2Ru_6C(CO)_{16}$ in 200 ml tetrahydrofuran was charged with synthesis gas ($H_2:CO=1:1$), heated to 275° C. and the pressure adjusted to 120 MPa. After 5 hours, the reaction was quenched by cooling. A gas chromatographic examination of the gas and liquid contents of the reactor indicated the formation 17 g of methanol and 3.8 g. of methyl formate. It is interesting to note the absence of hydrocarbon formation since ruthenium metal is well-known as a catalyst for hydrocarbon formation from synthesis gas.

What is claimed is:

1. A composition of matter comprising a bimetallic cluster compound of the formula $$L_2M_2Ru_6C(CO)_{16}$$

where L is RCN, R being $C_1$ to $C_6$ alkyl, $C_6$ to $C_{10}$ aralkyl or phenyl and M is copper, silver or gold.

2. The composition of claim 1 wherein L is $CH_3CN$, $CH_3CH_2CN$, $CH_3(CH_2)_2CN$, $(CH_3)_2CHCN$, $\phi CH_2CN$ or $\phi CN$.

3. The composition of claim 1 wherein M is copper.

4. The composition of claim 1 wherein the compound is $L_2Cu_2Ru_6C(CO)_{16}$.

5. A composition of matter comprising the compound $(CH_3CN)_2Cu_2Ru_6C(CO)_{16}$.

6. A process for preparing bimetallic cluster compounds of the formula $L_2M_2Ru_6C(CO)_{16}$ where L is RCN, R being $C_1$ to $C_6$ alkyl, $C_6$ to $C_{10}$ aralkyl or phenyl, and M is copper, silver or gold, which comprises reacting a solution of a ruthenium carbide cluster anion of the formula $[Ru_6C(CO)_{16}]^{2-}$ wherein the corresponding cation is alkali metal, alkaline earth metal, $N(R')_4{}^+$, $P(R')_4{}^+$ or $As(R')_4{}^+$ where R' is alkyl or aryl, with a Group Ib metal cation of the formula $M(L_4)^+$; M and L being defined above, in an inert organic solvent.

7. The process of claim 6 wherein the reaction is carried out in the absence of oxygen.